(12) United States Patent
Hirata et al.

(10) Patent No.: US 12,329,650 B2
(45) Date of Patent: Jun. 17, 2025

(54) ARTIFICIAL JOINT

(71) Applicants: Hitoshi Hirata, Nagoya (JP); Shigeru Kurimoto, Nagoya (JP); NIPRO CORPORATION, Osaka (JP)

(72) Inventors: Hitoshi Hirata, Nagoya (JP); Shigeru Kurimoto, Nagoya (JP); Shunsuke Notazawa, Osaka (JP); Yuto Otani, Osaka (JP)

(73) Assignee: NIPRO CORPORATION, Osaka (JP)

( * ) Notice: Subject to any disclaimer, the term of this patent is extended or adjusted under 35 U.S.C. 154(b) by 260 days.

(21) Appl. No.: 17/637,226

(22) PCT Filed: Aug. 21, 2020

(86) PCT No.: PCT/JP2020/031566
§ 371 (c)(1),
(2) Date: Feb. 22, 2022

(87) PCT Pub. No.: WO2021/033761
PCT Pub. Date: Feb. 25, 2021

(65) Prior Publication Data
US 2022/0273444 A1  Sep. 1, 2022

(30) Foreign Application Priority Data

Aug. 22, 2019 (JP) ................. 2019-152045
Aug. 22, 2019 (JP) ................. 2019-152093

(51) Int. Cl.
*A61F 2/42* (2006.01)
*A61F 2/38* (2006.01)
*A61F 2/30* (2006.01)

(52) U.S. Cl.
CPC .............. *A61F 2/4241* (2013.01); *A61F 2/38* (2013.01); *A61F 2/385* (2013.01);
(Continued)

(58) Field of Classification Search
CPC .... A61F 2/30767; A61F 2/385; A61F 2/4241; A61F 2002/30158; A61F 2002/30935;
(Continued)

(56) References Cited

U.S. PATENT DOCUMENTS 5,824,095 A    10/1998  Di Maio, Jr. et al.
6,454,808 B1 *  9/2002  Masada ................. A61F 2/4241
                                                    623/21.16

(Continued)

FOREIGN PATENT DOCUMENTS

FR    2 875 127 A1    3/2006
JP    2000-513245 A    10/2000
(Continued)

OTHER PUBLICATIONS

Jul. 19, 2023 Extended European Search Report issued in European Patent Application No. 20853674.8.
(Continued)

*Primary Examiner* — Suba Ganesan
(74) *Attorney, Agent, or Firm* — Oliff PLC (57) ABSTRACT

An artificial joint is characterized by: having a first member including a caput part on which a prescribed curved surface is formed, and a second member including a fossa part having a surface which abuts the prescribed curved surface of the caput part; the second member being rotatable in a flexing direction of a joint with a prescribed point on the caput part being the center of rotation; and the prescribed curved surface of the caput part being defined by a curve which depicts a convex arc toward the side abutting the fossa part when the caput part is viewed from the axial direction of the rotation, and in which, when two arbitrary points are taken on the curve, the radius of curvature of the point
(Continued)

positioned further toward the flexing side of the joint on the curve is smaller than the radius of curvature of the other point.

11 Claims, 5 Drawing Sheets

(52) U.S. Cl.
CPC .. *A61F 2002/30158* (2013.01); *A61F 2/30767* (2013.01); *A61F 2002/30935* (2013.01); *A61F 2002/4251* (2013.01)

(58) Field of Classification Search
CPC ............ A61F 2002/4251; A61F 2/3804; A61F 2002/3809; A61F 2002/3813; A61F 2002/3818; A61F 2002/3822; A61F 2002/3827; A61F 2002/3831; A61F 2/2836; A61F 2/384; A61F 2/3845; A61F 2/3854; A61F 2/3859; A61F 2002/3863; A61F 2/3868; A61F 2/3886; A61F 2/389; A61F 2/42; A61F 2/4261
See application file for complete search history.

(56) References Cited

U.S. PATENT DOCUMENTS

| | | | |
|---|---|---|---|
| 6,893,467 B1* | 5/2005 | Bercovy | ............... A61F 2/3868 623/20.14 |
| 9,872,771 B2 | 1/2018 | Tepic | |
| 2002/0065561 A1* | 5/2002 | Ogilvie | ................. A61B 17/15 606/87 |
| 2008/0039949 A1 | 2/2008 | Meesenburg et al. | |
| 2019/0117407 A1* | 4/2019 | Yang | ........................ A61F 2/38 |

FOREIGN PATENT DOCUMENTS

| | | |
|---|---|---|
| JP | 2004-520873 A | 7/2004 |
| JP | 2008-521524 A | 6/2008 |
| JP | 2019-510605 A | 4/2019 |

OTHER PUBLICATIONS

Oct. 20, 2020 International Search Report issued in International Patent Application No. PCT/JP2020/031566.

* cited by examiner

ARTIFICIAL JOINT

CROSS REFERENCE TO RELATED APPLICATIONS

This application is based upon and claims the benefit of priority of the prior Japanese Patent Application No. 2019-152045, filed on Aug. 22, 2019, and Japanese Patent Application No. 2019-152093, filed on Aug. 22, 2019, and International Patent Application No. PCT/JP2020/031566, filed on Aug. 21, 2020, the entire contents of which are incorporated herein by reference.

TECHNICAL FIELD

The present invention relates to an artificial joint used by being implanted in the human body.

BACKGROUND ART

For a situation in which joints are highly destroyed by various factors such as aging, trauma, inflammation, and tumor, total joint replacement is widely known as the most effective and most rational treatment means. For this reason, conventionally, in order to treat osteoarthritis caused by degeneration and abrasion of the cartilage of the joints of the four limbs, the degenerated joint is replaced with an artificial joint by a surgical operation.

Currently, an artificial joint generally used is designed on the basis of a so-called "anatomical shape" estimated by a manufacturer from a small number of skeleton samples and is mass-produced with several size variations.

More specifically, for example, an integrated type artificial joint is widely known, which has
- a stem embedded in each of adjacent bones with a degenerated joint interposed between them and a joint alternative portion made of a flexible member that enables bending of the joint (for example, Patent Literature 1).

In addition to the above, a so-called surface replacement type artificial joint is also known, which includes a member corresponding to the bone head portion of the bone on the proximal side of the joint to be replaced and another member corresponding to the receiving portion of the bone on the distal side facing the member on the proximal side (for example, Patent Literature 2).

However, the condylar joint, the hinge joint, the axle joint, and the like, have extremely large individual differences in joint shape, particularly, the shape of the condylar portion and the bone head portion, and hence the ranges of motion of many patients are limited due to shape mismatches, or artificial joints are loosened or damaged due to an excessive mechanical environment.

For example, the integrated type artificial joint made of a flexible member as in Patent Literature 1 allows the joint portion to bend due to flexibility but cannot hold the force upon bending the joint due the limitations on the range of motion. That is, the artificial joint merely serves as a bendable spacer. The durability of the artificial joint is also low, and it is necessary to perform a reoperation accompanying the breakage of the implant in a short period of time.

In addition, a surface replacement type artificial joint including a bone head side member and a receiving side member as in Patent Literature 2 uses a metal for the bone head side member and a hard resin for the receiving side member. This improves the problem of durability to some extent. However, since the shape of the joint surface is not appropriate and makes it difficult to preserve the tendons and the ligaments supporting the bending and stretching motion of the joint, the reproduction of the bending and stretching path of the joint is incomplete. As a result, the range of motion of the joint is narrowed.

On the other hand, in order to cope with this, in recent years, a "personalized artificial joints" has been developed which accurately imitates the original joint shape of a patient by applying a 3D printing technology and the like. However, in such a method, as a matter of course, large variations occur in the structure and characteristics of each product, and it is difficult to describe the mechanical performance. Accordingly, it is not reasonable even in industrial mass production.

In addition, when a surgery for replacing a joint with such an artificial joint is performed, it is a reality that ligaments, tendons, and the like around the joint are incised and excised in order to implant the artificial joint. However, in order to maintain the joint function and to recover early, it is desirable to preserve ligaments, tendons, and the like around the joint which can be preserved at the time of surgery as much as possible and restore the artificial joint to a place that the joint has been conventionally present after the implantation of the artificial joint.

For this purpose, it is desirable that the shape of the artificial joint be easy to preserve and restore the ligament and the tendon as much as possible and do not inhibit the functions of the preserved and restored ligament and the tendon. However, the conventional artificial joint does not necessarily have a shape that satisfies such needs.

CITATION LIST

Patent Literature

Patent Literature 1: JP 2000-513245 W
Patent Literature 2: JP 2008-521524 W

SUMMARY OF INVENTION

Technical Problem

In view of the above problems, an object of the present invention is to provide a general-purpose artificial joint that can reproduce a path close to the bending and stretching path of the normal limb joint and acquire the range of motion close to the healthy joint.

Solution to Problem

In order to solve the above problems, an artificial joint according to the present invention is an artificial joint used by being implanted in a human body and characterized by comprising a first member including a bone head portion on which a predetermined curved surface is formed and a first stem portion implanted in a first bone, and a second member including a bone fossa portion having a surface in contact with the predetermined curved surface of the bone head portion and a second stem portion implanted in a second bone adjacent to the first bone, wherein the second member is configured to pivot in a bending and stretching direction of a joint about a predetermined point on the bone head portion as a rotation center, and the predetermined curved surface of the bone head portion is defined by a curve that draws a convex arc toward a side abutting on the bone fossa portion when the bone head portion is viewed from an axial direction of the pivoting movement and has, when two arbitrary points are taken on the curve, a curvature radius at a point located closer to a bending side of the joint on the curve which is smaller than a curvature radius at another point.

In the present specification, the distal side means a side close to the fingertips of the four limbs, and the proximal side means a side close to the torso opposite to the distal side. The stretching side of the joint means the outside of a so-called joint, and similarly, the bending side means the inside of the joint. The stretching side of the joint is also referred to as "upper", and the bending side is also referred to as "lower".

In a configuration in which the spherical surface of the member that replaces the bone head of the bone has a single curvature radius in a state in which the artificial joint is implanted in the human body, it is not possible to obtain the range of motion similar to that of the original joint, and it is not possible to perform sufficient bending. In this respect, according to the above configuration, since the member that replaces the bone head has the curved surface defined by the curve whose diameter with respect to the rotation center decreases toward the bending side of the joint, the range of motion in the bending direction can be expanded as compared with the case of abutting on the spherical surface.

Further, the curve may be a curve constituting a part of the locus of a logarithmic spiral. According to such a configuration, the curved surface in the bone head portion can be more smoothly configured, and bending and stretching of the portion replaced with the artificial joint can be smoothly performed.

The curve may be a curve constituting a part of a locus of a logarithmic spiral defined by a Fibonacci sequence. According to such a configuration, a curved surface closer to the bone head of the living body can be configured, and the reproducibility of the bending and stretching path of the joint can be enhanced.

The bone head portion may include two convex condylar portions arranged in a direction perpendicular to the bending and stretching direction of the joint and a valley portion positioned between the two condylar portions, the bone fossa portion may include a central convex portion engaged with the valley portion and concave condylar receiving portions located on both sides of the central convex portion and engaged with the condylar portion, and the curved surface of the bone head portion may be formed at the condylar portion.

With such a configuration, it is possible to obtain a shape similar to the actual structure of the joint portion, and it is also possible to adjust the range of motion of the pivoting movement by adjusting the uneven shape of the abutment surface between the bone head portion and the bone fossa portion.

The valley portion may have a structure in which a stretching side of the joint is shallow and gradually deepens toward a bending side of the joint, and the central convex portion may have a structure in which a height gradually changes so that the stretching side and the bending side of the joint are high and a middle between the stretching side and the bending side is lowest.

With this configuration, as the joint changes from the bent state to the stretched state, the valley portion is restrained more greatly with respect to the central convex portion, and the restraint is maximized when the joint is in the stretched state. This prevents the second member from pivoting outward from the joint.

The bone fossa portion may be made of a metal. With such a configuration, since the thickness of the bone fossa portion can be reduced while a predetermined strength is maintained, it is possible to preserve the ligament around the joint, particularly the collateral ligament.

The bone fossa portion may have a side surface that forms a slope extending outward in the axial direction of the pivoting movement from a stretching side to a bending side of the joint. The bone fossa portion may have a substantially trapezoidal contour whose width of a lower portion is larger than a width of an upper portion when the bone fossa portion is viewed from the front. The front surface of the bone fossa portion refers to a surface abutting on a predetermined curved surface of the bone head portion. That is, "viewing the bone fossa portion from the front" means viewing from the side of the bone head portion which is in contact with the bone fossa portion.

When an operation of replacing the joint with the artificial joint is performed, it is desirable to preserve ligaments, tendons, and the like around the joint which can be preserved at the time of surgery as much as possible and restore the artificial joint to a place that the joint has been conventionally present after the implantation of the artificial joint. Accordingly, it is desirable that the shape of the artificial joint do not inhibit the function of the ligament or tendon that is preserved or restored.

For example, the lateral cord (extensor tendon) located across the distal and proximal sides of the finger joint is placed together on the upper side of the joint when the joint is stretched, and is divided into two and arranged on both side surfaces of the joint when the joint is bent. That is, the lateral cord slides on the side surface from the upper surface of the joint in accordance with the bending and stretching movement of the joint, but the conventional artificial joint does not allow such movement of the tendon (or ligament). In this respect, with the above configuration of the artificial joint according to the present invention, when the lateral cord is preserved and restored when the joint is replaced, the lateral cord can smoothly slide without hindering of movement. This makes it possible to smoothly perform the bending and stretching motion of the replaced joint.

In addition, the artificial joint may be applied to a joint that allows a human body to bend. For example, the present invention may be applied to a knee joint of a human body or may be applied to an elbow joint of a human body. In addition, the present invention may be applied to hand, ankle, and finger joints of a human body and may be further applied to a proximal interphalangeal joint or a metacarpophalangeal joint of a finger.

Advantageous Effects of Invention

The present invention can provide a general-purpose artificial joint that can reproduce a path close to the bending and stretching path of the normal limb joint and acquire the range of motion close to the healthy joint.

DESCRIPTION OF EMBODIMENTS

The present invention will be exemplarily described below based on embodiments with reference to the accompanying drawings. However, the dimensions, materials, shapes, relative arrangements, and the like of the components described in the embodiments are not intended to limit the scope of the present invention only to them unless otherwise specified. In the following description, the same reference numerals are used for the same elements, and redundant description will be omitted.

First Embodiment

Figure 1A:
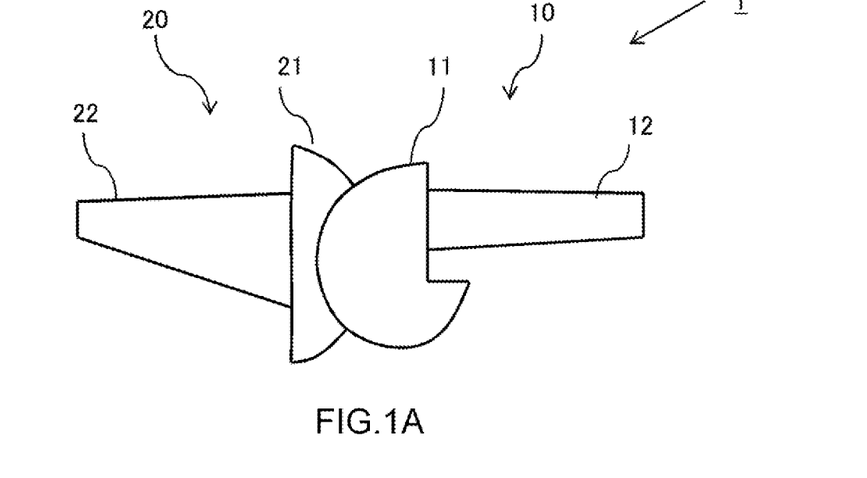
FIG. 1A is a side view schematically illustrating an artificial joint according to an embodiment.
Figure 1B:
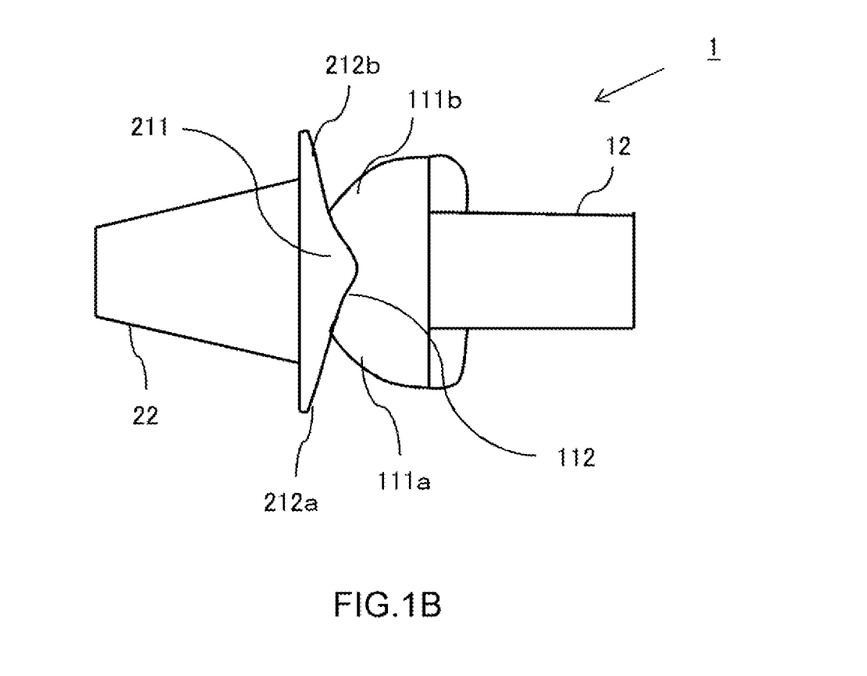
FIG. 1B is a plan view schematically illustrating an artificial joint according to an embodiment.

FIG. 1A and FIG. 1B schematically illustrate an artificial joint 1 according to the present embodiment. FIG. 1A is a side view of the artificial joint 1. FIG. 1B is a plan view of the artificial joint 1. The artificial joint 1 according to the present embodiment is an artificial joint that substitutes for a proximal interphalangeal joint (so-called second joint) of a finger and, as illustrated in FIG. 1A and FIG. 1B, includes a set of a proximal side member 10 arranged on a proximal phalanx side and a distal side member 20 arranged on a middle phalanx side.

The proximal side member 10 includes a bone head portion 11 that substitutes for a distal end portion of a proximal phalanx, and a proximal side stem portion 12 embedded in the proximal phalanx. The bone head portion 11 is preferably formed of, for example, a resin having excellent abrasion resistance such as ultrahigh molecular weight polyethylene. The effect of wear can be reduced when the bone head portion is combined with a distal side member having a metallic bone fossa portion.

In addition, the bone head portion 11 is configured to include two condylar portions 111a and 111b that are convex toward the distal side and a valley portion 112 positioned between them. The condylar portions 111a and 111b have curved surfaces defined by curves as described later, and the valley portion 112 has a structure in which the upper side is shallow and gradually deepens toward the lower side.

The distal side member 20 includes a bone fossa portion 21 that substitutes for a proximal end portion of the middle phalanx and a distal side stem portion 22 implanted in the middle phalanx. The bone fossa portion 21 is formed of, for example, a metal such as a cobalt-chromium alloy or pure titanium and can maintain strength even when the thickness is reduced.

Since the thickness of the bone fossa portion 21 can be formed thin, it is possible to preserve and restore more ligamentous attachment portions of the bone at the time of joint replacement surgery. This makes it possible to preserve more ligaments (and tendons) without removing them. This can accelerate the recovery of the joint function.

In addition, the bone fossa portion 21 includes a central convex portion 211 that engages with the valley portion 112 and concave condylar receiving portions 212a and 212b that are located on both sides of the central convex portion and respectively engage with the condylar portions 111a and 111b. The central convex portion 211 has a structure in which the height gradually changes so that the upper side and the lower side are high and the middle is the lowest.

The proximal side stem portion 12 and the distal side stem portion 22 may be configured to be implanted in the bone by a desired known technique and are formed of metal in the present embodiment.

Figure 2:
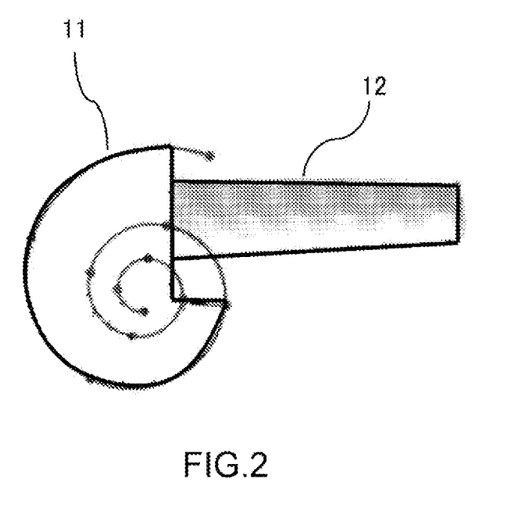
FIG. 2 is a view for explaining the shape of a condylar portion of the artificial joint according to the embodiment.

The condylar portions 111a and 111b of the bone head portion 11 each have a convex curved surface on the distal side, and the curved surface has a shape that is a so-called Fibonacci curve when the bone head portion 11 is viewed from the side surface as illustrated in FIGS. 1A and 2. The Fibonacci curve is a curve constituting a part of the locus of a logarithmic spiral (also referred to as a golden spiral) derived from the Fibonacci sequence. FIG. 2 is a view illustrating a golden spiral in a side view of the bone head portion 11 such that a part of the locus of the spiral overlaps a convex curve of the condylar portion 111a.

Figure 3A:
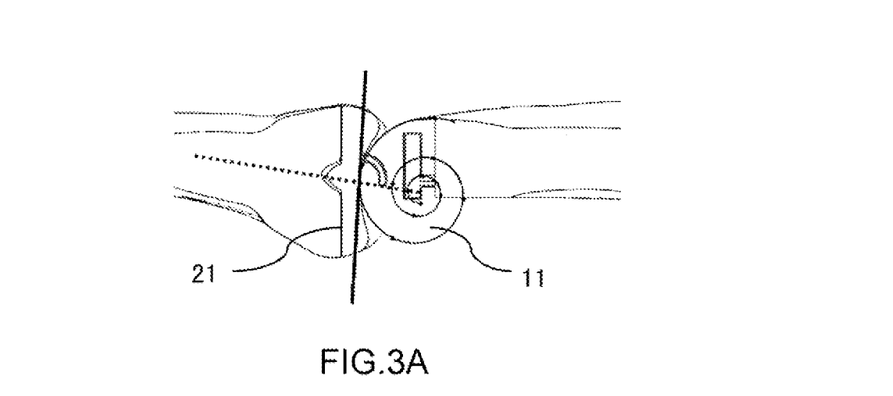
FIG. 3A is the first view for explaining the pivoting movement of the artificial joint according to the embodiment.
Figure 3B:
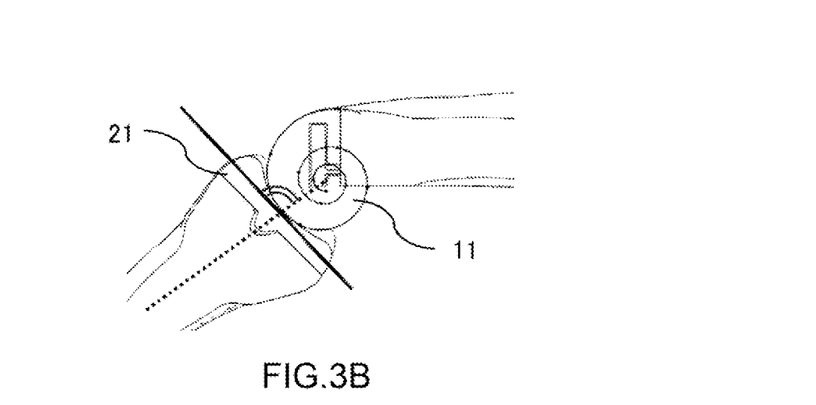
FIG. 3B is the second view for explaining the pivoting movement of the artificial joint according to the embodiment.
Figure 3C:
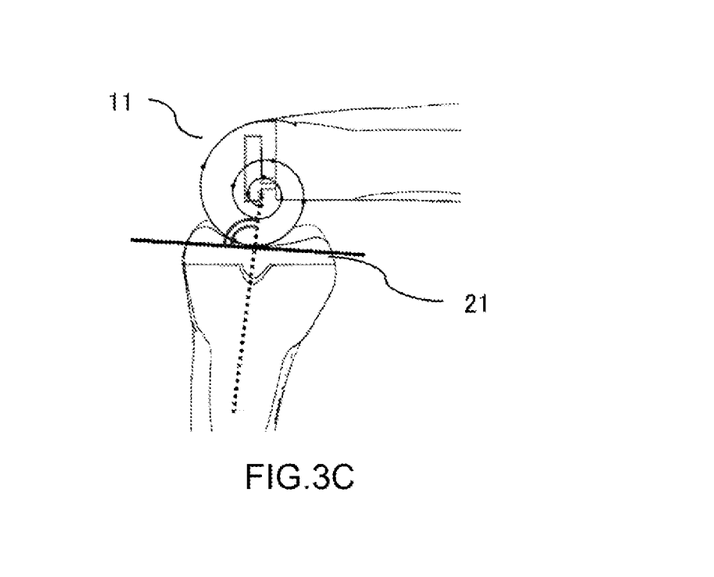
FIG. 3C is the third view for explaining the pivoting movement of the artificial joint according to the embodiment.

The distal side member 20 is vertically pivotal about a predetermined point on the bone head portion 11 of the proximal side member 10 as a rotation center and reproduces the bending and stretching motion of the finger by the pivoting movement. FIG. 3A, FIG. 3B, and FIG. 3C illustrate a state in which the distal side member 20 rotates about the rotation center of the bone head portion 11. FIG. 3A is a view illustrating a case in which the joint is in a stretched state (rotation angle is) 0°. FIG. 3B is a view illustrating a case in which the rotation angle is 45°. FIG. 3C is a view illustrating a case in which the joint is in a bent state. The spiral in FIG. 3A, FIG. 3B, and FIG. 3C indicate the above golden spiral.

The curved surfaces of the condylar portions 111a and 111b which abut on the distal side member 20 each are defined by a Fibonacci curve whose distance with respect to the rotation center of the bone head portion 11 decreases (that is, the radius of curvature decreases) toward the bending direction when the bone head portion 11 is viewed from a side surface (that is, the axial direction of the pivoting movement). Therefore, unlike the case of a curved surface defined by a curve that is an arc (that is, a part of the circle), the distal side member 20 can pivot more (for example, at a rotation angle of 100° or more) in the bending direction.

On the other hand, since the pivoting movement of the distal side member 20 is performed while the bone head portion 11 and the bone fossa portion 21 are in contact with each other, the distal side member 20 is prevented from pivoting upward from the horizontal direction by the configuration of the valley portion 112 and the central convex portion 211 as described above. More specifically, as the distal side member 20 pivots from the lower side to the upper side (the joint changes from the bent state to the stretched state), the valley portion 112 is restrained more greatly with respect to the central convex portion 211, and the restraint is maximized when the joint is in the substantially stretched state. This prevents the distal side member 20 from pivoting further upward.

In addition, the condylar receiving portions 212a and 212b of the bone fossa portion 21 are formed to engage with the condylar portions 111a and 111b without any gap at the position where the joint is in the stretched state and are formed such that a gap is slightly generated in the left-right direction at the position where the joint is in the bent state. Accordingly, the degree of freedom in the left-right direction can be obtained in a state where the joint is bent as in the case of a healthy joint.

Figure 4:
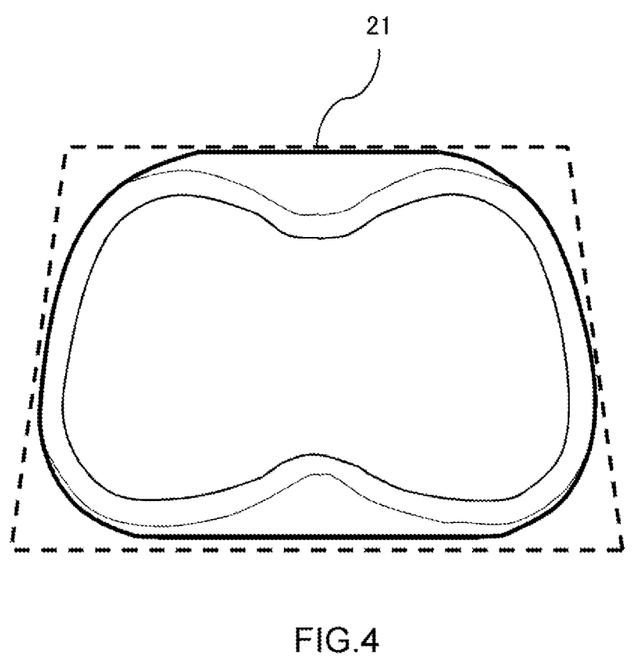
FIG. 4 is a front view illustrating the bone fossa portion of the artificial joint according to the embodiment.

FIG. 4 is a view illustrating a state in which the bone fossa portion 21 of the artificial joint 1 after being replaced as a joint in the human body is viewed from the front (that is, the surface on the side abutting on the bone head portion 11). The broken line in FIG. 4 indicates a trapezoid having an upper side shorter than a lower side. As illustrated in FIG. 4, when viewed from the front, the bone fossa portion 21 has a structure in which the width on the upper side is shorter than the width on the lower side, and both side surfaces have inclined surfaces expanding outward from the upper side to the lower side. That is, the bone fossa portion 21 has a substantially trapezoidal contour as indicated by the broken line in FIG. 4. Although not illustrated, the bone head portion 11 abutting on the bone fossa portion 21 also has a substantially trapezoidal shape when viewed from the front (that is, the surface on the side abutting on the bone fossa portion 21).

Figure 5A:
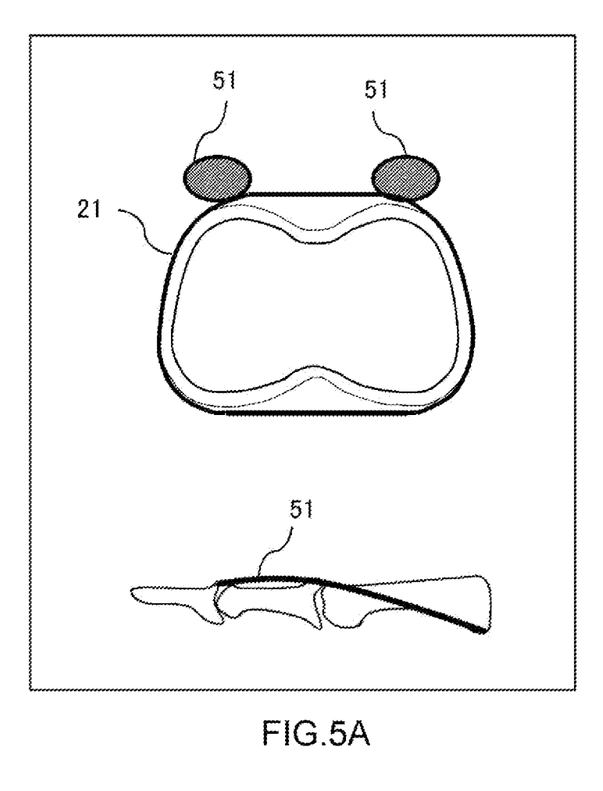
FIG. 5A is the first view illustrating the positional relationship between the bone fossa portion and the lateral cord accompanying the bending and stretching motion of a finger to which the artificial joint according to the embodiment is applied.
Figure 5B:
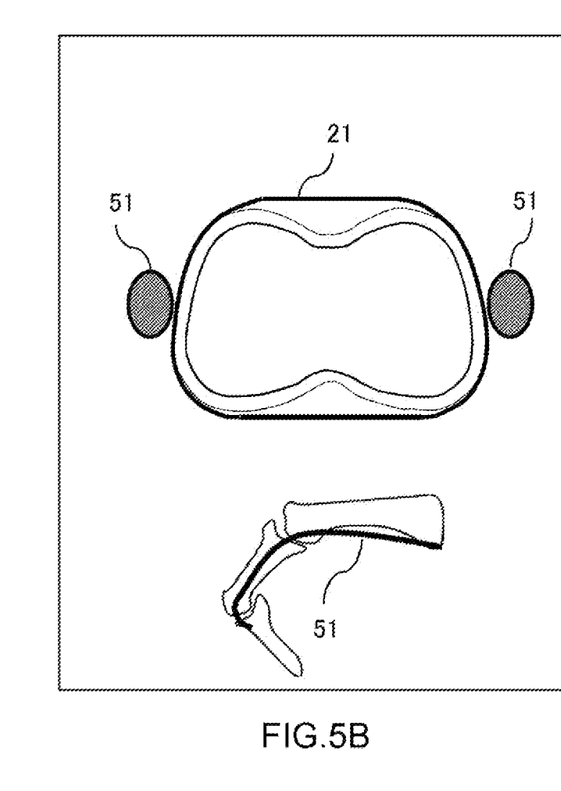
FIG. 5B is the second view illustrating the positional relationship between the bone fossa portion and the lateral cord accompanying the bending and stretching motion of the finger to which the artificial joint according to the embodiment is applied.

In a finger of the healthy living body, a lateral cord exists over the distal side and the proximal side of the joint and also functions as a tendon for bending the joint. FIG. 5A and FIG. 5B are views illustrating the positional relationship between the bone fossa portion 21 and the lateral cord 51 accompanying the bending and stretching motion of the finger to which the artificial joint 1 is applied. FIG. 5A is a view illustrating the positional relationship between the bone fossa portion 21 and the lateral cord 51 in a state where the joint is stretched. FIG. 5B is a view illustrating the positional relationship between the bone fossa portion 21 and the lateral cord 51 in a state where the joint is bent. As illustrated in FIG. 5A and FIG. 5B, the lateral cord 51 slides on the side surface from the upper surface of the joint in accordance with the bending and stretching motion of the finger, is arranged together on the upper side of the joint when the joint is stretched, and is divided into two and arranged on both side surfaces of the joint when the joint is bent.

Since the shapes of the bone fossa portion 21 and the bone head portion 11 are configured to have inclined surfaces extending outward from the upper side to the lower side on both side surfaces as described above, the sliding motion of the lateral cord from the upper surface to the side surface of the joint as described above is not hindered and smoothly performed, and thus the bending and stretching motion of the finger can be smoothly performed.

<Others>

Note that the description of the above embodiment is merely illustrative of the present invention, and the present invention is not limited to the above specific embodiment. The present invention allows various modifications and combinations of techniques within the scope of the technical idea. For example, the present invention can be applied not only to the proximal interphalangeal joint but also to an artificial joint of a finger such as a metacarpophalangeal joint. In addition, the present invention can be applied not only to the joint of the finger but also to an artificial joint of another joint of the four limbs of the human body such as an elbow joint and a knee joint.

The curves of the condylar portions 111a and 111b do not necessarily form a part of the locus of a golden spiral and may be any curves as long as the distance from the rotation center gradually decreases toward the bending side. In addition, the shapes of the bone fossa portion and the bone head portion when viewed from the front each are not necessarily trapezoidal and may be a substantially triangular shape.

REFERENCE SIGNS LIST 1 artificial joint
10 proximal side member
11 bone head portion
111 condylar portion
112 valley portion
12 proximal side stem portion
20 distal side member
21 bone fossa portion
211 central convex portion
212 condylar receiving portion
22 distal side stem portion
51 lateral cord

The invention claimed is:

1. An artificial joint for a human body, the joint comprising:
   a first member including a bone head portion, on which a predetermined curved surface is formed, and a first stem portion implantable in a first bone; and
   a second member including a bone fossa portion, which has a surface in contact with the predetermined curved surface of the bone head portion, and a second stem portion implantable in a second bone adjacent to the first bone, wherein
   the second member is configured to pivot in bending and stretching directions of a joint about a predetermined point on the bone head portion as a rotation center, and
   the predetermined curved surface of the bone head portion is defined by a curve that (i) is a convex arc toward a side abutting on the bone fossa portion when the bone head portion is viewed from an axial direction of pivoting movement, (ii) has, when two arbitrary points are taken on the curve, a curvature radius at a point located closer to a bending side of the joint on the curve which is smaller than a curvature radius at another point, and (iii) constitutes a part of a locus of a logarithmic spiral defined by a Fibonacci sequence.

2. The artificial joint according to claim 1, wherein the bone fossa portion has a side surface that forms a slope extending outward in the axial direction of the pivoting movement from a stretching side to the bending side of the joint.

3. The artificial joint according to claim 2, wherein the bone fossa portion has a trapezoidal contour with a width on the bending side larger than a width on the stretching side of the joint when the bone fossa portion is viewed from a surface side abutting on the predetermined curved surface of the bone head portion.

4. The artificial joint according to claim 1, wherein
   the bone head portion includes two convex condylar portions arranged in the axial direction of the pivoting movement and a valley portion positioned between the two condylar portions,
   the bone fossa portion includes a central convex portion engaged with the valley portion and concave condylar receiving portions located on both sides of the central convex portion and engaged with the condylar portion, and
   the predetermined curved surface of the bone head portion is formed at the condylar portion.

5. The artificial joint according to claim 4, wherein
the valley portion has a structure in which a stretching side of the joint is shallow and gradually deepens toward the bending side of the joint, and
the central convex portion has a structure in which a height gradually changes so that the stretching side and the bending side of the joint are high and a middle between the stretching side and the bending side is lowest.

6. The artificial joint according to claim 1, wherein the bone fossa portion is formed of a metal.

7. The artificial joint according to claim 1, wherein the artificial joint is a knee joint of a human body.

8. The artificial joint according to claim 1, wherein the artificial joint is an elbow joint of a human body.

9. The artificial joint according to claim 1, wherein the artificial joint is a finger joint of a human body.

10. The artificial joint according to claim 9, wherein the artificial joint is a proximal interphalangeal joint or a metacarpophalangeal joint.

11. The artificial joint according to claim 1, wherein the second member is configured to rotate 100 degrees or more in the bending direction.

\* \* \* \* \*